(12) United States Patent
Zainiev et al.

(10) Patent No.: US 6,458,456 B1
(45) Date of Patent: Oct. 1, 2002

(54) COMPOSITE FIBER FOR ABSORPTIVE MATERIAL CONSTRUCTION

(75) Inventors: Gafur Zainiev; Vladimir Gerasimov; Boris Zlotin, all of West Bloomfield, MI (US); Michael L. Weiner, Webster, NY (US)

(73) Assignees: Technology Innovations, LLC, W. Henrietta, NY (US); Ideation International, Southfield, MI (US)

( * ) Notice: Subject to any disclaimer, the term of this patent is extended or adjusted under 35 U.S.C. 154(b) by 0 days.

(21) Appl. No.: 09/532,613

(22) Filed: Mar. 22, 2000

Related U.S. Application Data

(60) Provisional application No. 60/125,677, filed on Mar. 22, 1999.

(51) Int. Cl.[7] .................................................. D05F 6/00
(52) U.S. Cl. ........................ 428/370; 428/376; 428/398
(58) Field of Search ................................. 428/376, 370, 428/373, 36.4, 374, 369, 400, 398, 394, 397

(56) References Cited

U.S. PATENT DOCUMENTS

| | | | | |
|---|---|---|---|---|
| 2,448,782 A | * | 9/1948 | Davis | 428/374 |
| 2,477,652 A | * | 8/1949 | Robbins | 428/370 |
| 3,616,149 A | * | 10/1971 | Wincklhofer | 161/89 |
| 4,247,393 A | * | 1/1981 | Wallace | 210/638 |
| 4,871,615 A | * | 10/1989 | Vigo et al. | 428/398 |
| 4,973,503 A | * | 11/1990 | Hotchkis | 428/36.4 |
| 5,057,368 A | * | 10/1991 | Largman et al. | 428/397 |
| 5,139,668 A | * | 8/1992 | Pan et al. | 210/321.8 |
| 5,456,982 A | * | 10/1995 | Hansen et al. | 428/370 |
| 5,580,459 A | * | 12/1996 | Power et al. | 210/631 |
| 5,725,949 A | * | 3/1998 | Pasquali et al. | 428/364 |
| 5,902,384 A | * | 5/1999 | Rohrbach et al. | 96/296 |
| 5,902,679 A | | 5/1999 | Kojima et al. | 428/375 |
| 6,004,673 A | | 12/1999 | Nishijima | 428/373 |
| 6,048,614 A | * | 4/2000 | Rohrbach et al. | 428/372 |
| 6,117,806 A | * | 9/2000 | Yokoi et al. | 501/135 |
| 6,127,036 A | * | 10/2000 | Xue et al. | 428/400 |
| 6,174,601 B1 | * | 1/2001 | Stanitis et al. | 428/373 |

* cited by examiner

Primary Examiner—N. Edwards
(74) Attorney, Agent, or Firm—Townsend and Townsend and Crew LLP; Fidel D. Nwamu

(57) ABSTRACT

An absorbent fiber is constructed to include a hydrophobic exterior and a hydrophilic interior for use in various absorbent constructions as an absorbent, capture and entrain liquids and attendant odors.

13 Claims, 14 Drawing Sheets

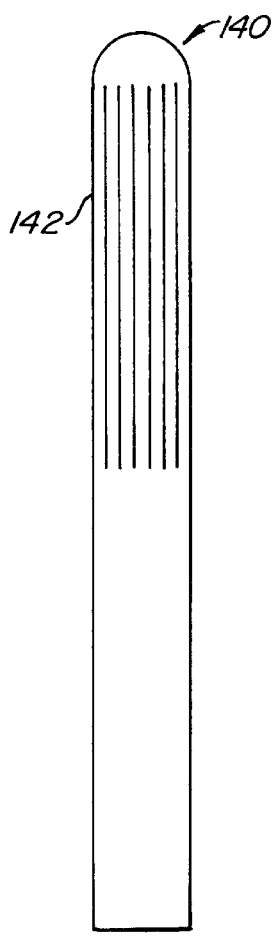
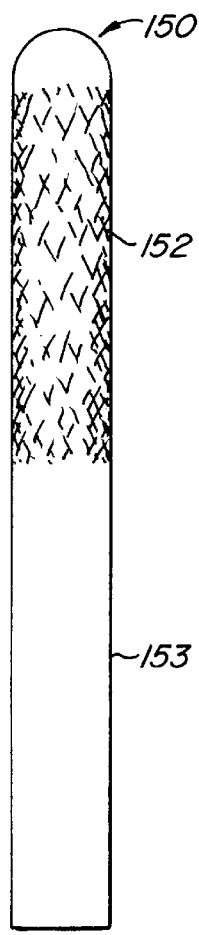
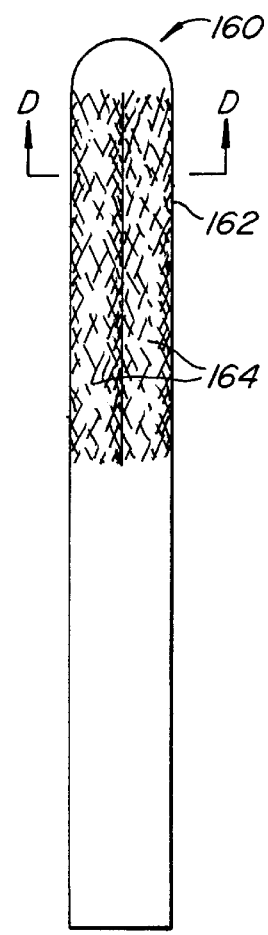
FIG. 15.    FIG. 16.    FIG. 17A.
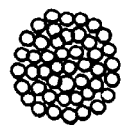 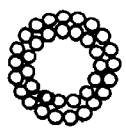 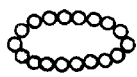 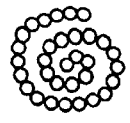 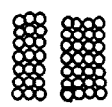
FIG. 17B.   FIG. 17D.   FIG. 17F.   FIG. 17I.   FIG. 17K.
 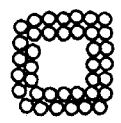   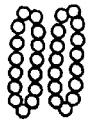
FIG. 17C.   FIG. 17E.   FIG. 17G.   FIG. 17J.   FIG. 17L.

FIG. 20A.
FIG. 20B.
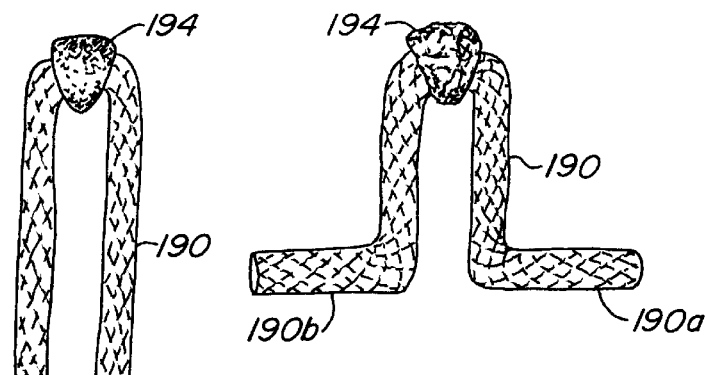
FIG. 20C.
FIG. 20D.
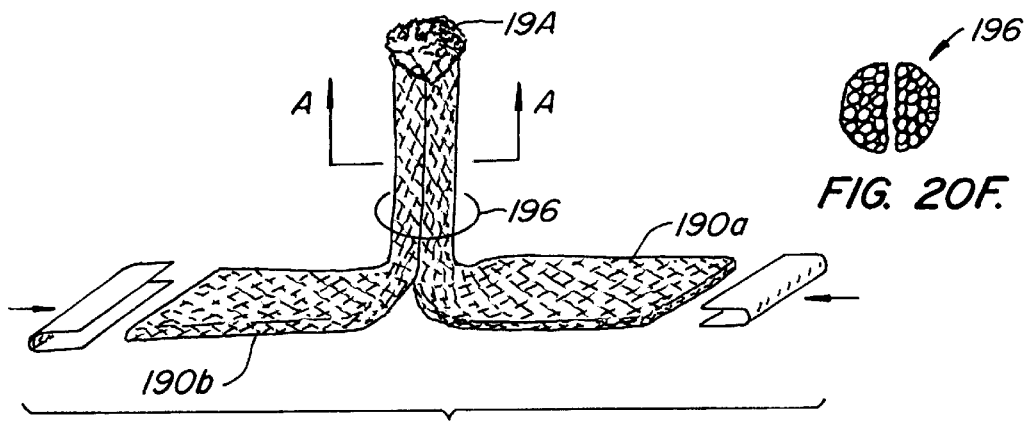
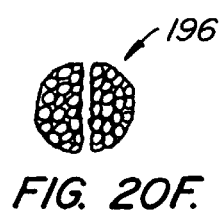
FIG. 20F.
FIG. 20E.

COMPOSITE FIBER FOR ABSORPTIVE MATERIAL CONSTRUCTION

CROSS-REFERENCES TO RELATED APPLICATIONS

This application claims priority to co-pending U.S. Provisional Patent Application No. 60/125,677, filed Mar. 22, 1999, the disclosure of which is incorporated herein in its entirety for all purposes.

BACKGROUND OF THE INVENTION

The present invention relates generally to absorptive materials, and more particularly to construction of an absorbent composite fiber having an enhanced fluid absorptive and retentive capability as well as relating to use of the absorbent composite fiber for absorbent article constructions such as diapers, pads, surgical dressings and like articles.

The field of absorbent products has seen continual improvement over the years, realizing absorbent materials and products made from those materials with improved containment. Prior technologies have generally used a shared relationship between the thickness of an absorbent article and the absorbent capacity of that article. For example, thickening the material of an article in order to increase its absorbency can result in a concomitant reduction in comfort when the article is worn. Solutions to problems at the interface between absorbency and comfort have included a reduction in the thickness of the material used, but often with an accompanying reduction of absorbency; alternatively, greater absorbency (and retention) is achieved at the cost of thicker, bulkier constructions. Thus, even though tremendous improvements have been made over the years in this field, offering materials with greater absorbency and improved coatings, personal use absorbent article constructions have nonetheless continued to be relatively thick and, therefore, somewhat uncomfortable when used. The addition of bulk to enhance absorbency for some absorbent constructions, such as adult briefs for bladder-bowel control (i.e., adult diapers), can interfere with normal clothing, and can be a cause of embarrassment. Too, although the fluid retentive abilities of such constructions can be quite good, their odor retention capabilities can be lacking, again creating a possible social embarrassment—particularly for older adults.

Adults, being more sensitive to the social issues associated with odors, appreciate the confidence of being able to go into a workplace, or a social situation, or engage in an athletic activity, without fear of leakage, or odor escapement, and with longer periods of time between changes.

The present invention provides an improvement over the current technology in addressing many of these concerns.

SUMMARY OF THE INVENTION

The present invention is first directed to an absorbent fiber having both hydrophilic and hydrophobic qualities. Embodiments of the invention utilize the absorbent fiber for the construction of various articles with enhanced absorptive abilities and retention of both liquid and attendant odors.

Broadly, one aspect of the present invention is directed to an absorbent fiber constructed to absorb and entrain a liquid by capillary action. In addition to absorption and retention of the liquid, the capillary action afforded by the absorbent fiber functions to retain odors that may be associated with the absorbed liquid. In one embodiment of this aspect of the invention the fiber is constructed from a liquid impervious material, such as plastic, rubber, or other like material, forming an elongate, hollow tube. The fiber is dimensioned to permit the operation of capillary action for liquid recovery and retention. In one embodiment of the invention, the absorbent fiber is a composite construction in which the interior of the fiber includes an absorbent, hydrophilic material to enhance absorbency and retention of both liquids and odors. In addition, the material of such a composite absorbent fiber may be of a type that can crystallize or otherwise harden when wet in a manner that permits such material furthest from the fiber's point of absorption will harden or crystallize first to thereby seal and contain the absorbed liquid. Alternatively, other materials may be included in the interior of the fiber to add a thinning property to the liquid being absorbed to enhance absorption.

In another embodiment of the invention, the composite construction of the absorbent fiber may constructed by using a woven fabric or material to form the tube-like exterior of the fiber for housing one or another of the absorbent materials. The weave can be chosen to adjust the rate of liquid absorption and retention.

The absorbent fiber of the present invention lends itself to being combined with, or to include, various monitoring devices so that, therefore, further embodiments of the invention have included in the interior of the absorbent fiber sensor devices capable of providing an indication of the amount of liquid absorbed, and/or when the article employing the fiber is reaching its absorbent capacity.

Further, the absorbent fiber of the present invention finds particular advantage when used as a liquid communicative bridge or connector between a site of absorption and a reservoir for liquids collected at the absorption site. Accordingly, the absorbent fiber of the present invention may connect to reservoirs formed as pads that can be strapped to or otherwise inconspicuously be carried by the user, or to a colostomy bag. Also, the reservoir may be formed as an article that can be worn, such as an undershirt. Further still, the reservoir can be permanently affixed to the absorptive element, or removably connected so that the reservoir can be removed and replaced with another reservoir when the first has reached its storage capacity.

The absorbent fibers of any of the aspects of the invention may be used alone, or in combination with other fibers, and is particularly adapted to the construction of such articles as disposable diapers, incontinence pads, sanitary napkins, tampons, headbands, absorbent vests, panty liners, underpants, undershirts, sweatshirts, socks, or any other garment or articles requiring absorption and containment of bodily or other fluids. And, when so used, the fibers may be apertured along their lengths to permit the admission of liquids. Absorbent fibers of the present invention so apertured can be included in an article that can advantageously placed only at the source of the liquid or bodily fluid to be absorbed without fear that the absorbed liquid may leak from other portions of the fiber.

There are a number of advantages achieved by the present invention. An article using the absorbent fiber of the present invention can provide an absorbing ability without the bulk or odor of prior devices and articles. The retention of absorbed liquid by capillary action in a liquid impervious tube will ensure that the liquid and its attendant odor cannot escape.

The tubular construction of the either the hollow or composite fiber allow for the implantation of a liquid-responsive material in the tube of the absorbent fiber to initiate action in the presence of the absorbed liquid such as triggering the release of anti-allergens, or anti-bacterial, or the like.

Further, absorption by capillary action permits products to be constructed with greater absorbing capacity than heretofore available. The use of capillary action provides the ability to transport absorbed liquids to locations remote from the source of the liquid being absorbed, greatly extending the life between changes of absorbent products. Thus, such products as tampons, diapers, colostomy bags, and the like, when made from the composite absorbent fiber of the present invention, can be worn or used longer before removed and/or replaced.

These and other object s and advantages of the present invention will become apparent to those or ordinary skill in this art upon a reading of the following detailed description of the invention, which should be taken in conjunction with the accompanying drawings.

BRIEF DESCRIPTION OF THE DRAWINGS

FIGS. 10–22 illustrate use of the invention in various tampon constructions;

DETAILED DESCRIPTION OF THE SPECIFIC EMBODIMENTS

Figure 1:
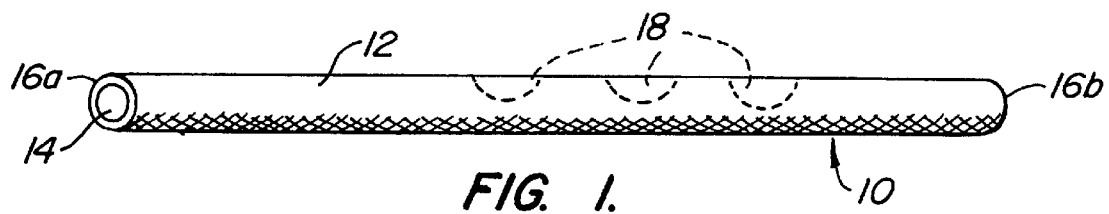
FIG. 1 is an illustration of an absorbent fiber constructed according to the teachings of the present invention.

Turning now to the figures, and for the moment specifically FIG. 1, there is illustrated a basic construction of an absorbent fiber according to the present invention. As shown, the absorbent fiber, designated generally with the reference numeral 10, is in the form of a hollow tube fabricated to have an impervious, hydrophobic or nonabsorbent tube-like exterior 12 and dimensioned to provided a hydrophilic or absorbing interior 14. The absorbent fiber 10 is preferably constructed and dimensioned so that the interior 14 is made hydrophilic through capillary action, and may be constructed of a plastic, rubber, or other liquid impervious and material. Also, it is preferable, although not necessary, depending upon use of the absorbent fiber 10, that is be constructed to have some flexibility.

The absorbent fiber 10 may be used in conjunction with conventional fibers (e.g., cotton, nylon, wool, and the like) for the construction of an absorbent article, i.e., an absorbent pad, a diaper product, a sanitary napkin, or an article of clothing. The absorbent fibers 10 will have opening, such as the ends 16a, 16b, located in the absorbent article so that when placed to absorb liquids, such as bodily fluids of one type or another, the apertures are located at or near the source of the fluid. Alternatively, the fiber 10 may be apertured at locations along its length such as indicated in phantom at 18 for permitting the ingress of fluid to the fiber 10. Because of the capillary action, ingress is enhanced, as is the retention and containment of the fluid absorbed by the fiber 10 while minimizing annoying wetness to the wearer. This is an important advantage of the invention, and is due, at least in part, to the liquid impervious construction of the fiber 10.

Figure 2A:
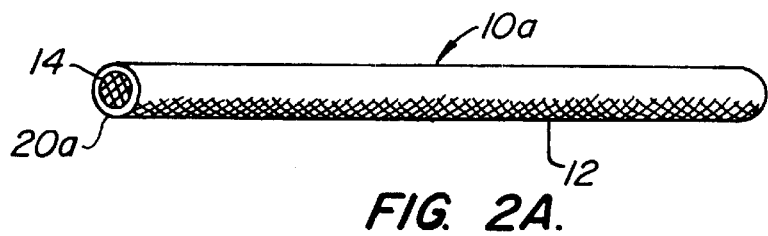
FIGS. 2A–2H are alternate constructions of the absorbent fiber of FIG. 1, illustrating the construction of a composite fiber according to the teachings of the present invention.
Figure 2B:
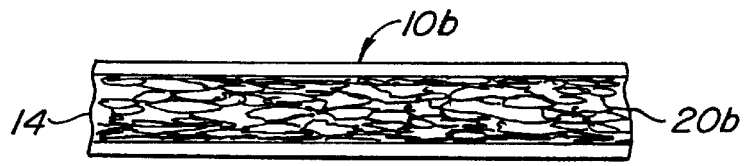
Figure 2C:
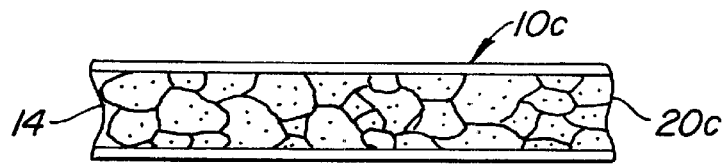
Figure 2D:
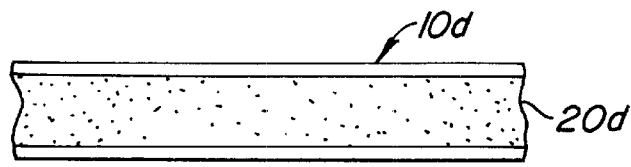

FIGS. 2A–2H various alternate embodiments of the absorbent fiber 10 of the present invention, forming various composite absorbent fibers. Certain of the absorbent and composite constructions illustrated in FIGS. 2A–2H use the same absorbent fiber 10 construction illustrated in FIG. 1 and will, therefore, use the same reference numerals. FIG. 2A shows, for example, an absorbent fiber 10a using a hydrophobic tube with an absorbent filler 20a contained in the interior 14. The filler 20a could be strands of cotton fiber, wool fiber, or other material. For example, FIG. 2B shows an absorbent fiber 10b with a filler 20b in the form of a fibrillar glass fiber. Alternatively, as illustrated in FIG. 2C, a composite absorbent fiber 10c is shown containing a filler 20c contained within the interior 14 can be porous granules of one type or another such as $Al_2O_3$, $SiO_2$, coal powder, or other porous materials utilized as catalysts support. Similarly, FIG. 2D shows a composite absorbent fiber 10d containing a filler 20d in the form of granular substance such as a hydrophilic "sand" which may be a glass powder or a like material that is much finer than the larger, porous granules 20c shown in FIG. 2C.

Figure 2E:
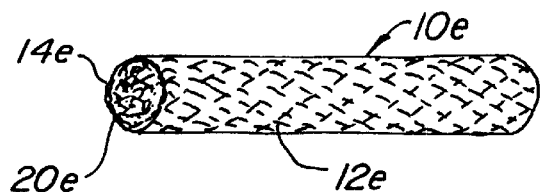

FIG. 2E shows a somewhat different construction for an absorbent fiber according to the present invention. Here, the absorbent fiber, identified in FIG. 2E as absorbent fiber 10e, is a tubular construction formed by a weave of preferably hydrophobic or nonabsorbent threads 12e which may be hydrophobic plastics, polyethylene, or the like. A composite structure is created by providing the interior 14e with absorbent filler material 20e, which can be any of those described above. Ingress to the interior 14e of the composite absorbent fiber 10e may be provided through the weave pattern, depending upon the tightness of the weave, which permits such the ingress to be adjusted according to how loose or how tight the weave is. Leakage out of fiber 10e can start only after of internal absorbent becomes saturated, making the capacity of fiber 10e limited.

Figure 2F:
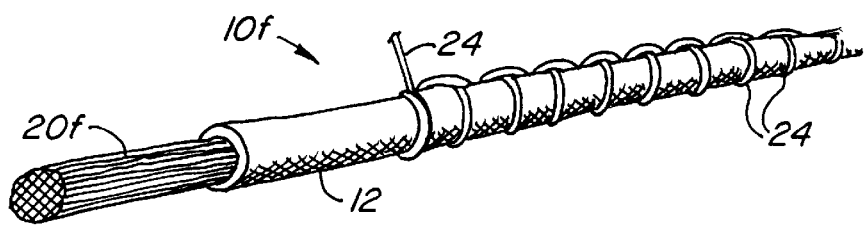

In FIG. 2F, a composite absorbent fiber 10f uses the hydrophobic tube 12 filled with a number of smaller absorbent, hollow fibers as filler 20f to form the composite structure. In addition, the composite absorbent fiber 10f is shown in FIG. 2F with thread 24 wrapping the filler 20f. The thread 24 may be such material as cotton or other soft fabric, to enhance the softness of the composite construction, and thereby raise its comfort when used in an absorbent article. Further, the composite absorbent fiber shown in FIG. 2F may alternatively contain any of the fillers 20 described above in conjunction with FIGS. 2A–2D rather than the smaller absorbent fibers 20f.

Figure 2G:
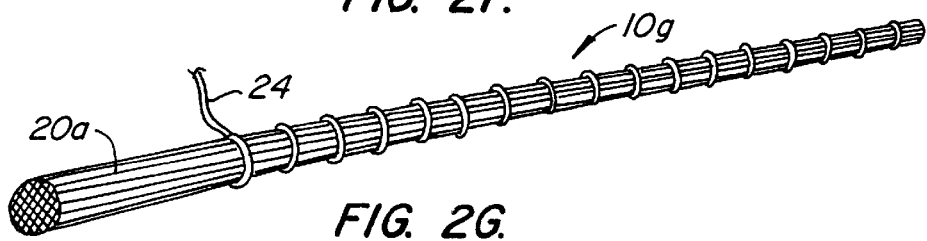

FIG. 2G illustrates a still further construction of an absorbent fiber according to the present invention. As FIG. 2G shows, a composite absorbent fiber 10g is formed using only the absorbent threads 20a, used in the composite construction of FIG. 2A, wrapped and held together by thread 24' in much the same manner as shown in FIG. 2F. Thereby, a composite absorbent fiber 10g is created. As described above, the filler threads 20a can be cotton, wool, or even nylon fibers, or fibers formed from other materials whether man-made or natural. The thread 24' used to form the absorbent fiber 10g similarly may be any material, but since the thread 24' is to provide a comfort aspect to the composite fiber 10", the thread 24 preferably is a soft material.

Figure 2H:
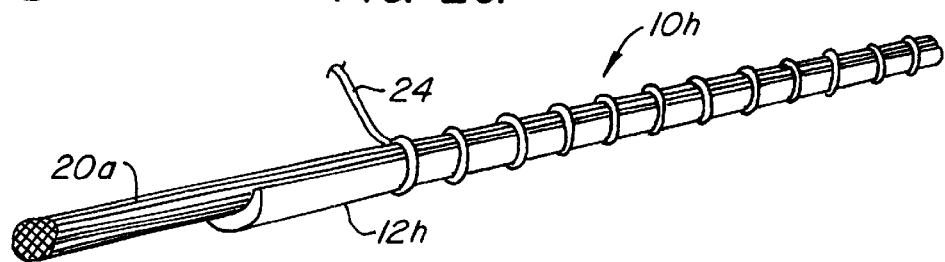

Finally, in FIG. 2H there is illustrated a composite fiber 10h constructed to include the absorbent threads 20a with an elongate half section tube 12h forming a kind of trough to hold the absorbent threads 20a. The thread 24 wraps the absorbent threads 20a to hold them in the concave area of half-tube 12h as shown in FIG. 2H.

Figure 3A:
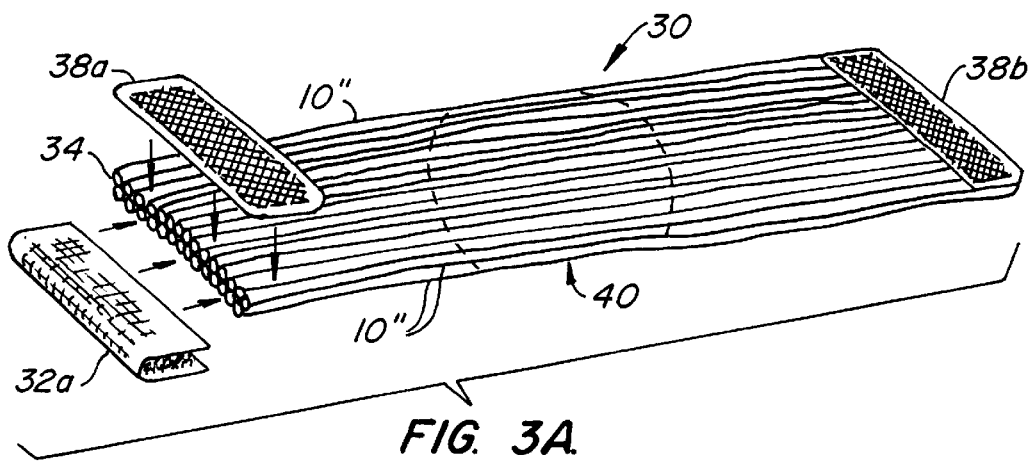
FIGS. 3A and 3B illustrate an absorbent article constructed using the teachings of the present invention.
Figure 3B:
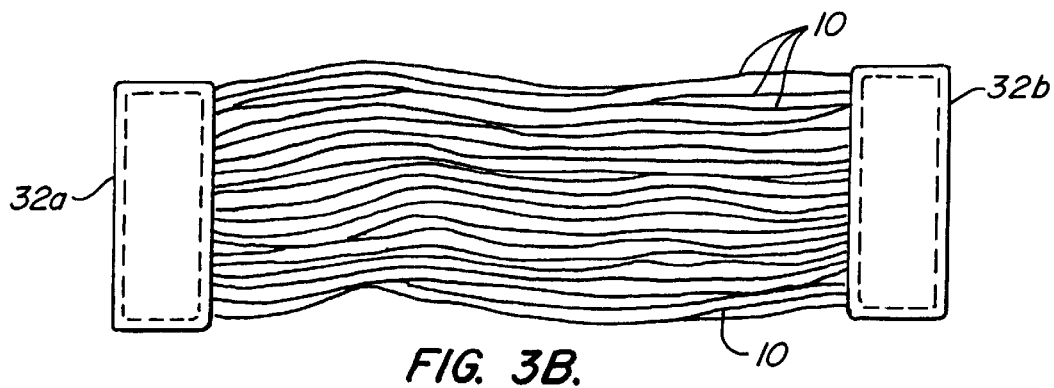

Turning now to FIGS. 3A and 3B, a use of the present invention is illustrated. As FIGS. 3A, 3B show, a plurality of absorbent fibers 10" are placed in parallel relation, alone or along with other conventional fibers, to form an absorbent pad 30 that may be used as a sanitary napkin, adult diaper, or anything of the like. As illustrated, the absorbent pad 30 includes end pieces 32a, 32b, which attach to, and hold, the ends 34 of the fibers 10. Although not shown, the end pieces 34 may contain an absorbent material, such as cotton, to provide a reservoir for liquids absorbed by the absorbent fibers 10". The absorbent fibers 10" may be any of the constructions shown in FIGS. 1 or 2 (2A–2H), and may be combined, if desired, with conventional material.

The pad 30 may take on various shapes. For example, the pad may have less length than illustrated in FIG. 3, but contain more absorbent fibers for more width to make it a more rectangularly shaped pad. Alternatively, if the pad were to be used as, for example, a sanitary napkin or diaper construction, whether for children or adults, the pad may be constructed from longer fibers 10", making it a bit more elongate in shape and form. Affixed to the end pieces 32, either by sewing or by gluing or other affixation means, is one part of a hook and mate construction 38 (38a, 38b) such as Velcro brand material, allowing the pad 30 to be removably attached to under garments (which would contain the mating half of the elements 38).

Also, the pad 30 would be preferably apertured along the lengths of the absorbent fibers 10", much like the apertures 18 in FIG. 1, to permit fluid flow to the interior of the absorbent fibers 10" in the area 40 (shown in phantom) of the pad 30. Alternatively, the area 40 may include an ingress construction such as illustrated in FIG. 2H, in which a portion of the fibers is cut away to permit ingress. Or, the fibers themselves may be of a weave such as shown in FIG. 2E with the weave being looser in the area that will be placed in juxtaposed relation to the fluid source.

Figure 4A:
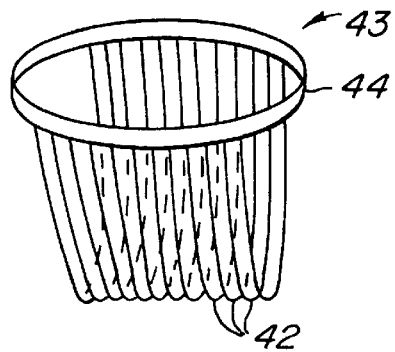
FIGS. 4A–4B, 5A–5B, and 6A–6B illustrate an absorbent diaper construction using the teachings of the present invention.
Figure 4B:
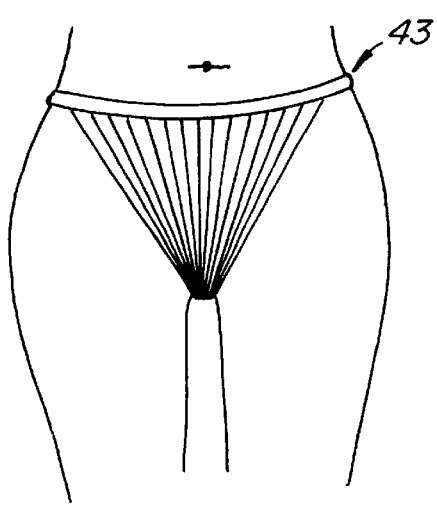

FIGS. 4–6 show use of a number of absorbent fibers 42 to construct a thong-like panty 43 for use as a sanitary napkin or adult diaper. FIG. 4A, for example, shows the fibers 42, which may be of any of the constructions described above, attached at their terminus to a waistband 44. Preferably, the fibers 42 would be apertured along their length, either in the manner shown in FIG. 1, or FIG. 2H, at locations that will place them (the apertures) proximate the source of fluid. To extent the fluid absorbing capability of the panty 43, the waistband 44 may contain an absorbent material to entrain fluids transported thereto by the absorbent fibers 42.

Figure 5A:
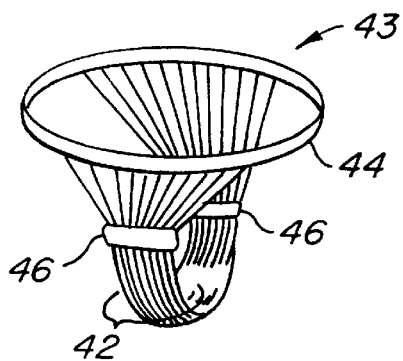
Figure 5B:
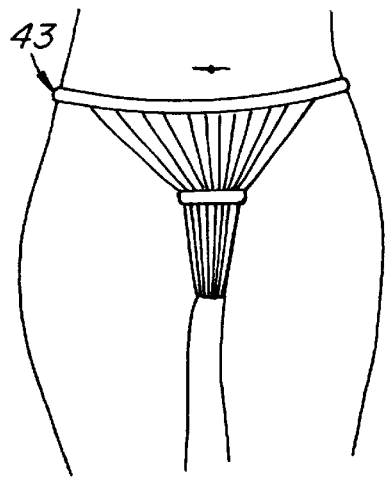

FIG. 5A shows the absorbent filaments 10 gathered together by elements 46, front and back, and its use as shown in FIG. 5B.

Figure 6A:
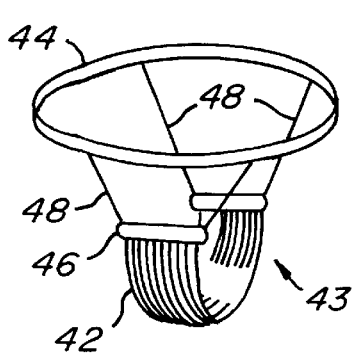
Figure 6B:
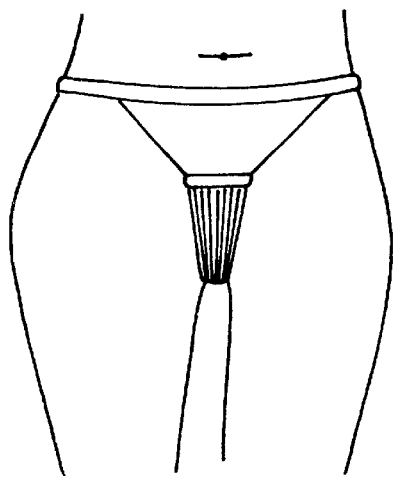

FIG. 6A shows the panty 43 with the ends of the absorbent 42 terminating at an attachment element 46. The element 46, in turn, is connected to the waistband 44 by support fibers 48. The support fibers 48 may be constructed using any of the absorbent fibers constructions of FIGS. 1 and 2, thereby providing a transport for fluid to the waistband 44. Use of the construction illustrated in FIG. 6A is then shown in FIG. 6B.

As mentioned in connection with the discussion of FIG. 4A, the waistband 44 of the panty 43 shown in FIGS. 4, 5, and/or 6 could itself serve as a reservoir for absorbed, entrained fluids. Thus, the absorbent fibers can be connected or otherwise affixed to the waistband 44 to provide fluid communication thereto for storage of fluids absorbed by the absorbent fibers 42. The waistband 44 itself could be a larger construction of that shown in FIGS. 4–6 in that it may have a fluid impervious outer shell that enclosed an absorbent material for entrainment of fluids conveyed thereto by the fibers 42.

An advantage of the constructions illustrated in FIGS. 4–6 is that they provide an absorbent article that is minimally noticed under clothing, yet with an extended storage capability particularly when the waistband 44 is part of the absorbing mechanism.

Figure 7A:
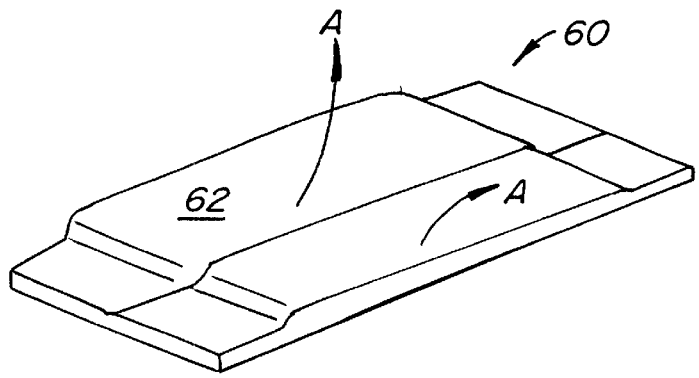
FIGS. 7A–7D illustrate using an absorbent fiber according to the teachings of the present invention in a sanitary napkin or diaper construction.
Figure 7B:
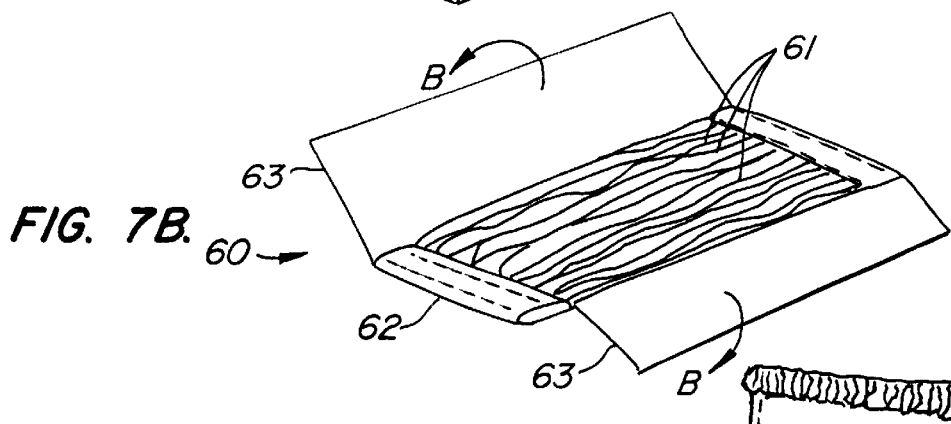

FIGS. 7A–7D illustrate yet a further embodiment of the invention, using any of the absorbent fiber constructions illustrated in FIGS. 1 and 2. As shown in FIGS. 7A and 7B, an absorbent pad 60 is constructed using a plurality of the absorbent fibers 61 contained in a cover 62. As FIGS. 7A and 7B illustrate, the cover 62 is formed with flaps 63 that close over the absorbent fibers 61 of the pad 60 to protect them. The flaps 63 may then be moved, as illustrated by the arrows A, A (FIG. 7A) and B, B (FIG. 7B), to expose the absorbent fibers 61 for use. Again, depending upon the use of the pad 60, the absorbent fibers 61 may be apertured at specific locations along their length, so that the pad 60 can be positioned to place the apertures of the fibers 61 proximate the source of fluid (e.g., wound, or other bodily opening or orifice).

Figure 7C:
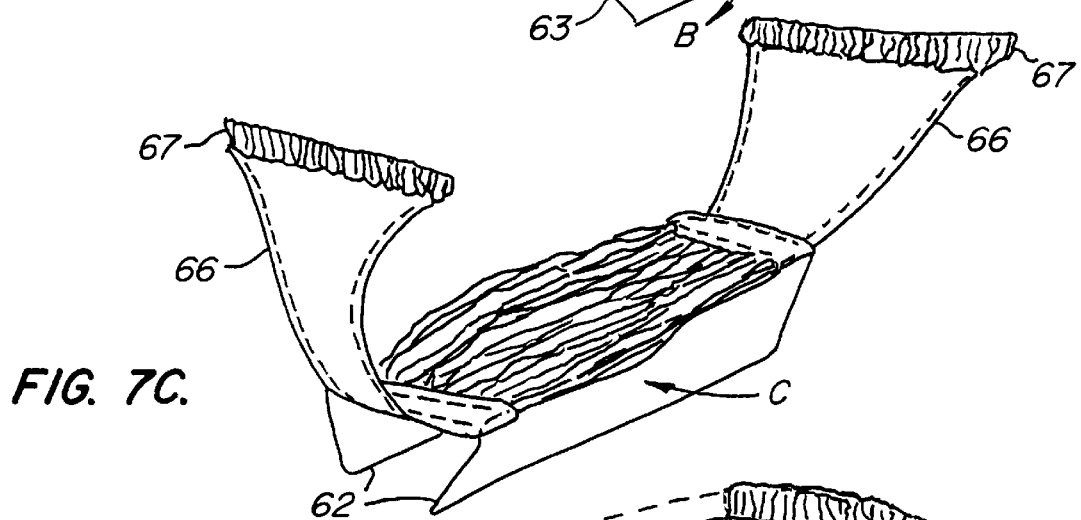
Figure 7D:
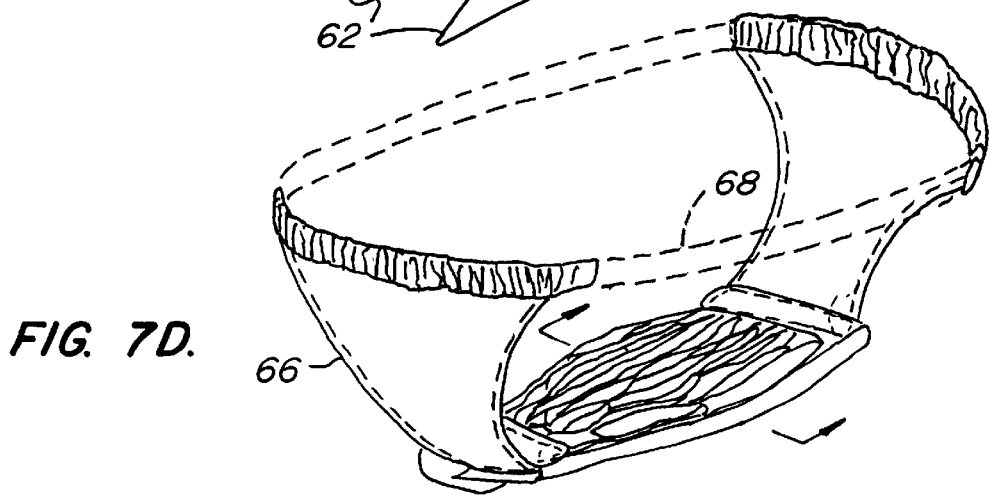

FIGS. 7C and 7D show pad construction 60 further including front and rear elements 66 so that the pad 60 may be used as a sanitary napkin or diaper. In FIG. 7C, the terminal portions 67 of the elements 66 may form an affixation means 67 to allow the pad 60 to be attached and worn with and undergarment. Alternatively, the terminal portions 67 may be formed to attach to or form a part of a waistband 68 (FIG. 7D) for wear.

If the pad 60 is to be worn with underwear, the cover 62 operates to protect the underwear by being positioned between the underwear and the absorbent fibers 61. In addition, the flaps 62 may be folded beneath the main body of the construction 60, capturing a bottom portion of the undergarment 66 to hold the construction 60 in place.

Further, the elements 66, including the waistband 68, could themselves may include absorbent fibers, having substantially the same construction as the absorbent fibers 61, and in fluid communication with the fibers 61, to provide additional reservoir capacity for absorbed fluids. The fibers making up this additional reservoir would be formed from fibers as shown in FIG. 1, with a liquid impervious shell or outer construction to entrain the fluid it receives yet remain dry outside.

Figure 8A:
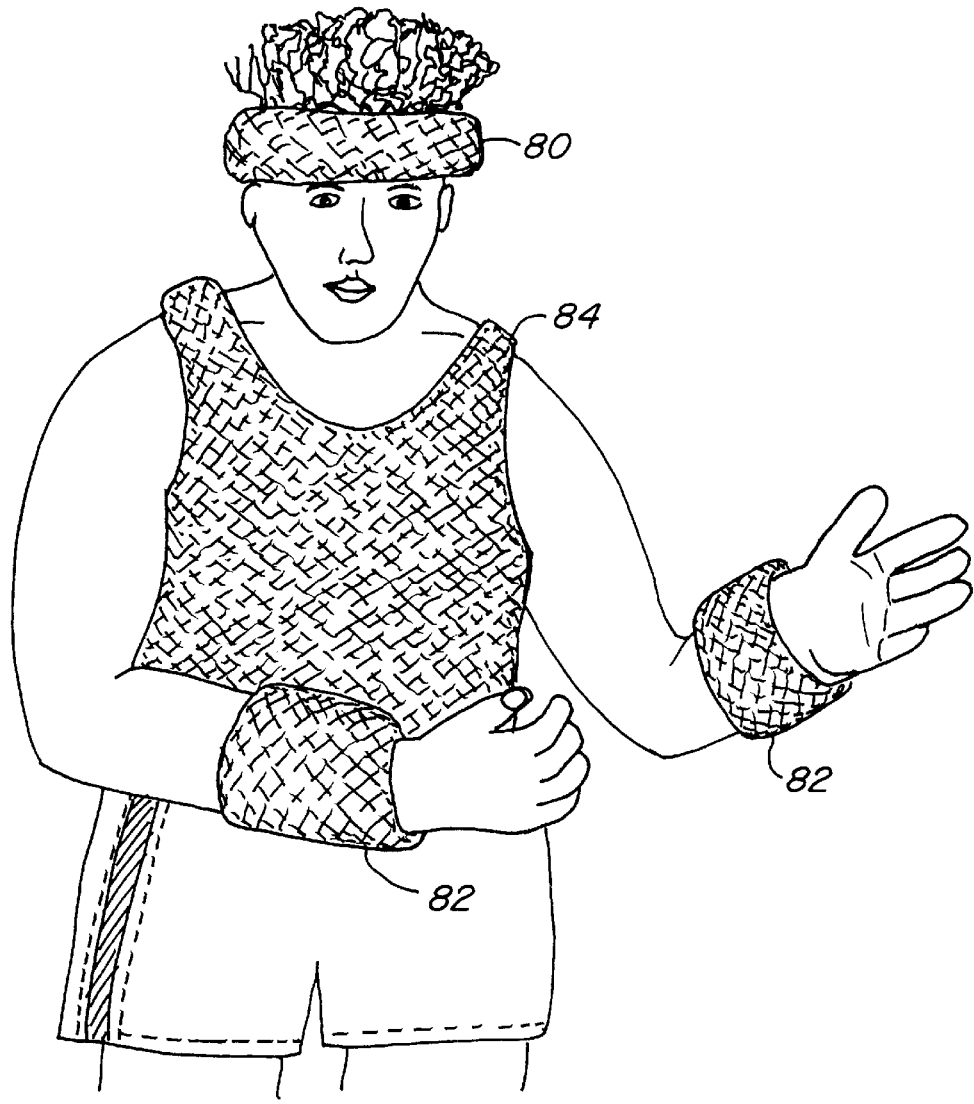
FIGS. 8A and 8B show embodiments of the invention employed to absorb perspiration.
Figure 8B:
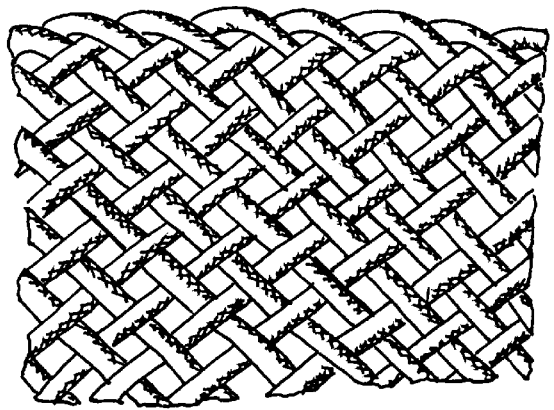

FIGS. 8A and 8B illustrate yet another use of the absorbent fiber of the present invention. FIG. 8A shows use of the invention to construct an absorbent headband 80, absorbent wrist bands 82, and an absorbent top 84. Preferably, the material used to construct the headband 80, wrist bands 82 and/or the top 84 is a woven fabric as shown in FIG. 8B using an of the absorbent fiber or absorbent composite fiber constructions illustrated in FIGS. 1–2. The absorbent fibers used in the construction of the articles 80, 82, 84 are preferably apertured appropriately along their lengths to permit ingress to the fiber of liquid (i.e., perspiration). Alternatively, the absorbent fibers used may be of the woven construction such as shown in FIG. 2e in which case the interstitial spaces between the fibers of the weave provide the ingress. Also, the absorbent fibers used for the construction of the articles 80, 82, 84 may be interwoven by themselves, or with other, more conventional absorbent materials, such as cotton or wool.

Figure 9A:
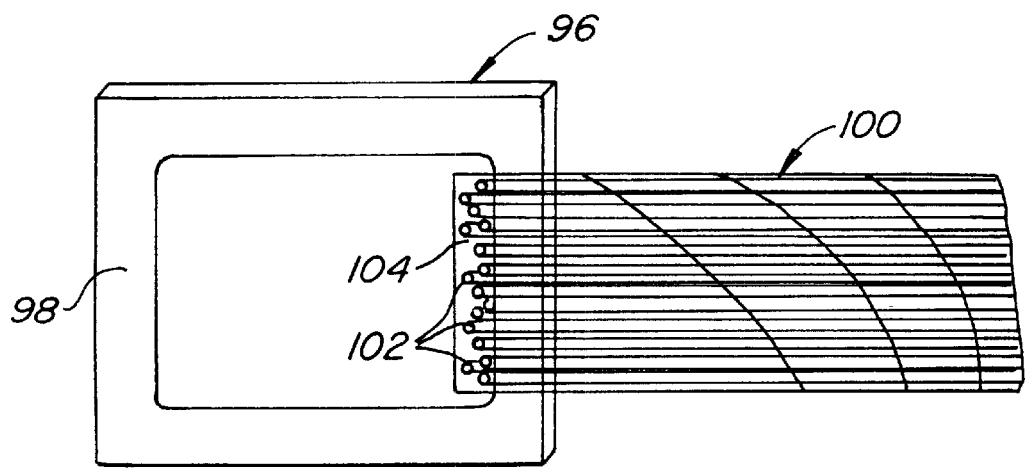
FIGS. 9A and 9B illustrate the composite absorbent fibers of the present invention to form a reservoir that can extend the absorbent capability of various absorbent articles.
Figure 9B:
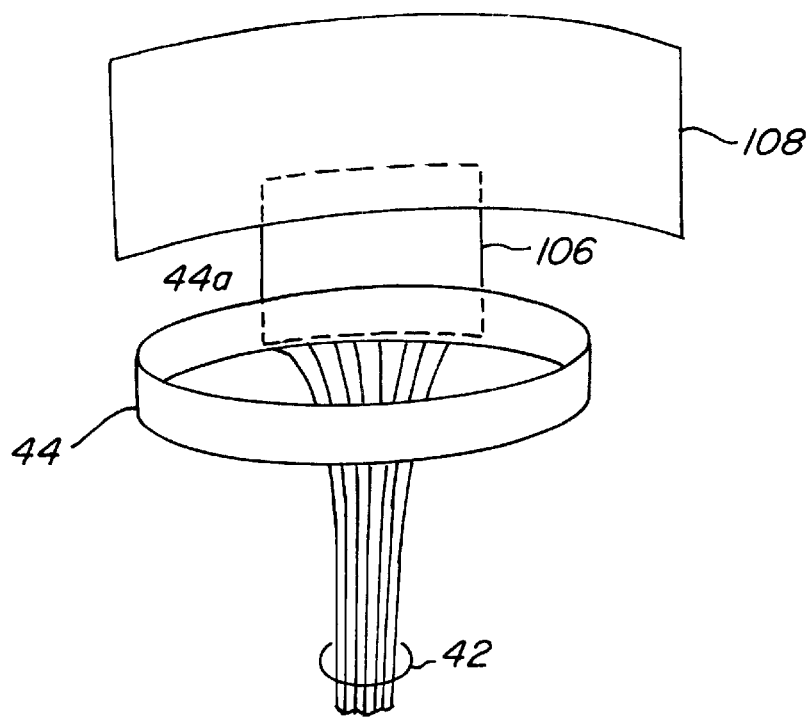

FIGS. 9A and 9B show ways of using the absorbent fiber of the present invention to form a reservoir, extending the absorbing capacity of an article. FIG. 9A illustrates an absorbent construction, such as a wound covering 96, which may be fabricated from conventional wound absorbing material, such as cotton. The wound covering 96 includes a peripheral adhesive 98 for affixing the wound covering 96 in place on a person (e.g., covering a wound). The adhesive material 98 also covers and holds the ends of absorbent fibers 100 constructed as described above that together form a fluid reservoir. The ends 102 open in a packed area 104 of the wound covering 96 so that fluids absorbed by the absorbent material of the wound covering 96 are presented to the openings 102 where absorption into the absorbent fibers 100 by capillary action can occur. Fluids presented to the openings 102 can then transported from the wound covering 96 for entrainment in a medium removed from the source of the fluids being absorbed. The absorbent fibers 100 may be of any length so as to comfortably fit to the user. For example, the absorbent fibers 100 might be of a length to extend around the waist of a person or partially around the waist of a person, or along their arm, etc., and be tied, taped, woven, or otherwise affixed to the body or clothing adjoining the wound or other area covered by the wound covering 96. Also, the absorbent fibers 100 can be removably attached to the wound covering 96 by various types of snap connectors.

The structure of the absorbent article illustrated in FIG. 9A may also be advantageously used by persons who have had an ostomy. The covering 96 can be modified to fit and the stoma to collect such discharges as may be encountered, depending upon the particular ostomy (e.g., a colostomy, ileostomy, or urostomy). The collected discharge can then be absorbed by the absorbent fibers 100, which acts as a reservoir (e.g. colostomy appliance). Alternately, the absorbent fibers 100 can operate as a conduit to transport the collected discharge from the covering 96 to a remote location where a larger reservoir may reside.

FIG. 9B illustrates use of the reservoir concept in conjunction the sanitary napkin or adult diaper construction discussed above and shown in FIGS. 4–6. As FIG. 9B shows, waistband 44 which holds absorbent fibers 42, connects at 44a to a set of absorbent fibers 106. The set of absorbent fibers 106 will, in turn, connect a reservoir 108. As explained above, fluids absorbed by the absorbent fibers 42 of the sanitary napkin or adult diaper construction will, by capillary action, be transported to the waistband 44. From there, again by capillary action, the fluid will be absorbed into the set of absorbent fibers 106 for conveyance to the reservoir 108. The reservoir 108 may be a pad, sweater or other configuration, of any shape or length or construction, able to retain additional fluids. The 108 reservoir might be traditional absorbent material contained in a liquid impervious material, or it could be a garment or pad made of one or more of the composite absorbent fibers of the present. FIGS. 9A and 9B illustrate, therefore how absorbent materials using composite fibers can be connected together to allow for movement and retention of fluids and containment of odors by a series of elements connected together by a variety of means as desired for the optimal configuration. The connection point 44a depicted between the waistband 44 and the set of absorbent fibers 106 may be aided by the use of Velcro, tape, stitching, glue, string, or any other means of mating. The reservoir 108 be taped to the body, or connected to other garments, or can be wrapped around in full or partial configuration and secured by a string.

Figures 10, 11, 12, 13, 14:
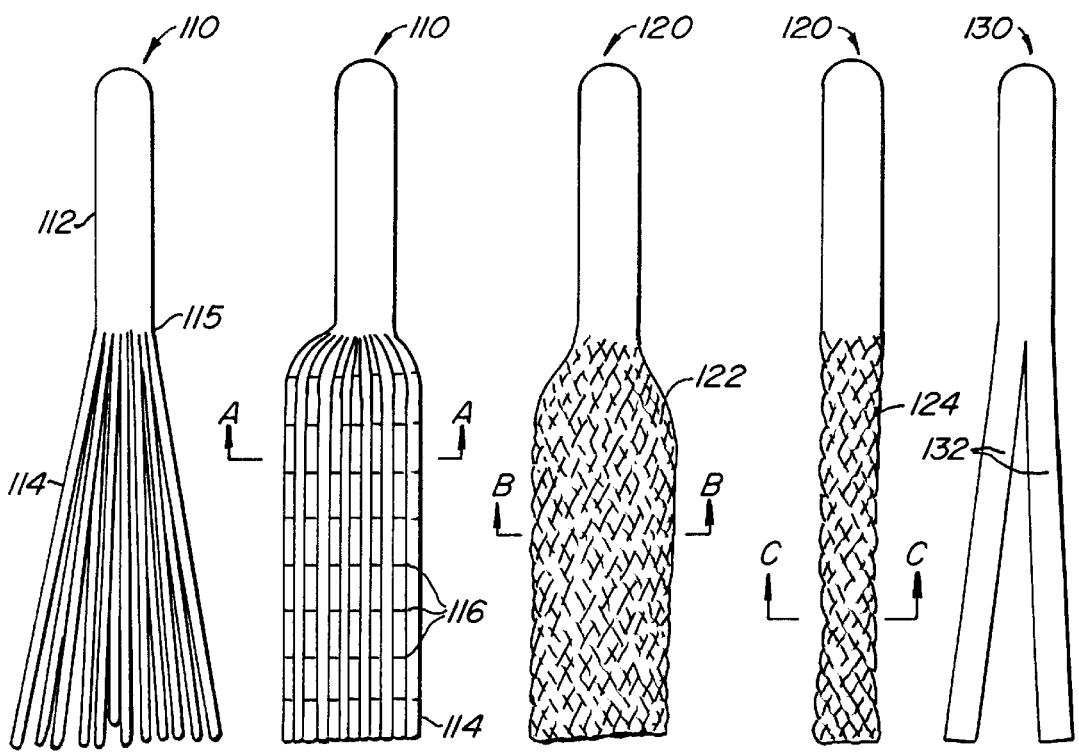

Turning now to FIGS. 10–22, there are illustrated various constructions of tampons employing the composite absorbent fiber of the present invention. Referring first to FIG. 10, a tampon 110 is shown having an insertion component 112 and a reservoir portion 114 comprising a plurality of composite absorbent fibers 10 of the present invention. The insertion component may be made from conventional absorbent material or from composite absorbent fibers of the present invention, or it may be made of a combination of both. If made of the inventive composite absorbent fibers, the fibers are merely extended to form the reservoir section 114. Conversely, if the insertion component 112 is formed from conventional absorbent materials, the absorbent fibers making up the reservoir component 114 would attached to the insertion component at 115 by any means so that the open ends of the absorbent fibers forming the reservoir 114 are positioned to absorb, by capillary action, fluids from the insertion component 112.

However constructed, the reservoir component 112 would, of course, be positioned to hang loosely outside of the body of the user when the insertion component is in place. The reservoir component could then be folded to lie flat in a panty or similar article of clothing. Fluids absorbed by the insertion component 112 are transported to the reservoir component 114 for entertainment, thereby extending the period of time that the tampon 110 can be used without changing.

Figure 11A:
Figure 11B:
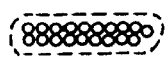
Figure 11C:

FIG. 11 shows the tampon 110 with the absorbent fibers 114 of the reservoir component gathered and held together by stitching 116 to hold them in a compact grouping. The particular means of affixing the absorbent fibers of the reservoir component may be by stitching, or a glue or tape method of attaching the fibers may be used, one to the next, in this case laterally, so as to form a desired grouping. FIGS. 11A–11C illustrated some of the groupings of fibers, which can be made when, viewed along the line A—A of FIG. 11. FIG. 11A, for example, shows grouping the absorbent fibers of the reservoir component in a single row, using single fibers, forming a relatively flat reservoir construction that will lie flat in a panty. Or, as FIG. 11B shows the absorbent fibers can be grouped as double fibers attached one to the next forming two rows of absorbent fibers. FIG. 11C illustrates yet another possible grouping, showing three rows of fibers. The particular shape and configuration of the reservoir 114 of the tampon can depend upon use, and such factors as how long the tampon will be used before changing. For example, in a hospital setting, the more bulky construction of the reservoir 114 shown in FIG. 11C may be preferred, whereas for use by someone more active, the construction shown in FIG. 11A will be the one selected.

FIG. 12 shows the tampon, here designated with the reference numeral 120, with the composite absorbent fibers forming the reservoir component 122 are interwoven to for a cross-hatch weave. The reservoir component 122 can be constructed solely of absorbent fibers of any of the composite absorbent fiber constructions described above, or it can be constructed by inter-weaving such composite absorbent fibers with conventional absorbent materials. Again, the reservoir component 122 may be provided with any of the cross-sectional shapes shown in FIGS. 11, or any other cross-sectional shape.

Figure 13A:
Figure 13B:
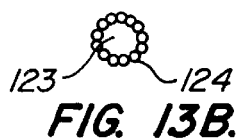
Figure 13C:

FIG. 13 illustrates forming the reservoir component 122 of the tampon 120 is a similar interwoven construction, but in a circular manner to gather the absorbent fibers to form such cross-sections as in FIG. 13A, showing the composite absorbent fiber cluster. FIGS. 13B and 13C show that the absorbent fibers forming the reservoir 124 can be arranged to define a hollow interior 123 or 125, respectively. Any of the configurations shown in FIGS. 11, 12, or 13 may also be contained in an outer shroud of plastic or film for additional fluid and other retention.

Finally, FIG. 14 shows the tampon, designated 130, having two ribbon shaped composite absorbent fibers 132. These are designed so as to redistribute, collect and retain discharges in a variety of means designed to adjust to body shape and size, and may optionally connect to underwear or panty liners or other garments.

FIGS. 15–17 show additional tampon constructions 140, 150 and 160, respectively. Here, the insertion component of the tampon is made with composite absorbent fibers, conventional materials, or a combination of the two. The construction of the tampon can be in a variety of cross-sectional shapes (FIGS. 17B, . . . , 17L). Some shapes that the insertion components 142, 144, 146 of the tampons 140, 150, 160, respectively, can take include packed shapes (FIG. 17B), some hollow (FIGS. 17C–17F), some round (FIGS. 17B–17D), some square (FIG. 17E), some oval (FIG. 17F), and some rectangular (FIGS. 17E and 17G), are shown. These designs provide a variance in absorbency and capillary effect.

FIG. 15 shows a tampon 140 formed with individual composite absorbent fibers, which may take on any of the cross-sectional configurations shown in FIGS. 17J, 17K, or 17L, or for that matter, and of the cross-section shown in FIGS. 17B–17G. The particular cross-sectional configurations used, of course, also depend upon the anatomy with the tampon will be used.

FIG. 16 shows a tampon 150 with the absorbent fibers interwove to form both the insertion component 152 and the reservoir 153. Alternatively, the insertion component may be only conventional absorbent woven material that attaches to the absorbent fibers of the present invention that make up the reservoir 153 of the tampon 150

The tampon 160 (FIG. 17A) shows a tampon formed from a pair of columns 164 of composite absorbent fibers gathered by stitching or any other means to hold them together. The cross-sectional configurations of the tampon 160 are shown in FIGS. 17J–17L.

Figures 18A, 18B, 18C, 18D, 18E, 18F:
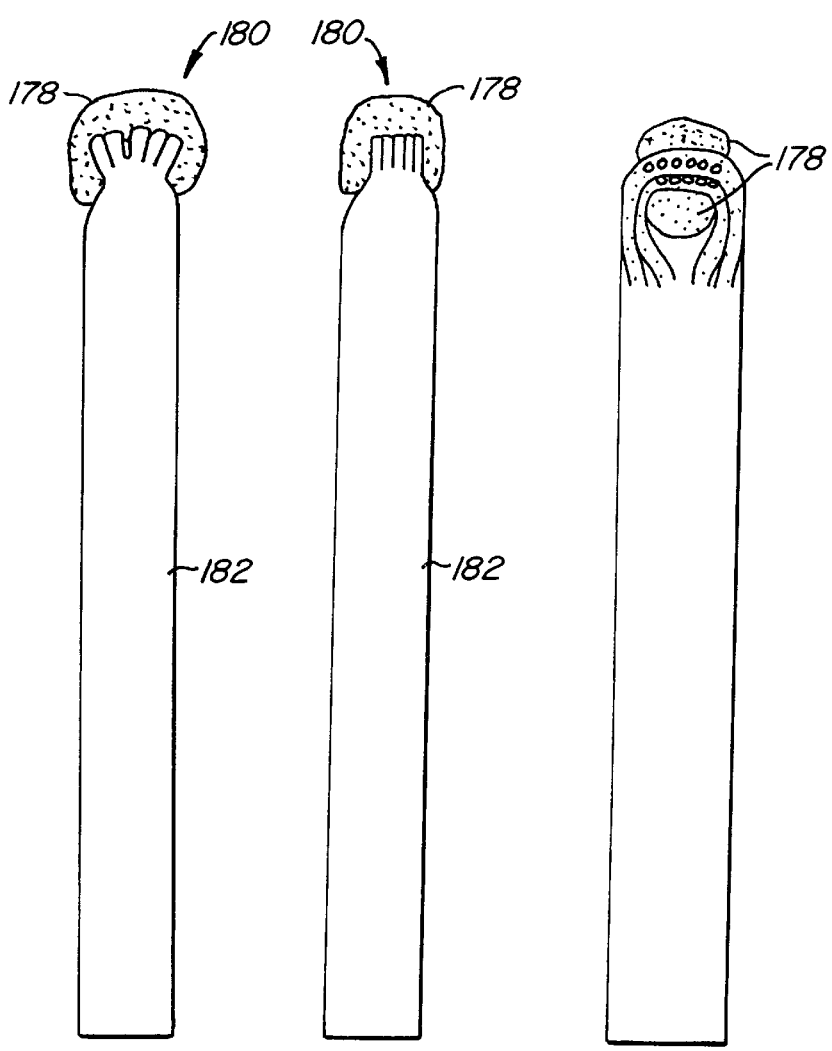

Turning now to FIGS. 18 (FIGS. 18A, 18B, . . . , 18F), there is illustrated yet another tampon construction incorporating the teachings of the present invention. FIGS. 18A–18C illustrate construction of the tampon. FIG. 18A shows a bundle 170 of absorbent fibers 168 constructed as described above. The absorbent fibers 168 are provided apertures proximate the center of their lengths as shown at 172. Then, as shown in FIG. 18B, a swath 174 of absorbent material, such as cotton, is wrapped around the absorbent fibers 168, covering the apertures 174. The absorbent fibers 168 are then bent in the direction of arrows D—D, as illustrated in FIG. 18C, and wrapped in an outer layer of material, excluding the absorbent material 178, forming the tampon construction 180 illustrated in FIGS. 18D–18F. Since the major effluent will be from the uterus, only the top portion of the tampon need be absorbent. There is no need to absorb fluids from the vagina walls, allowing a variety of selections of materials to be used as the wrap for the body 182 of the tampon 180. The absorbent fibers 168 form the tampon 180 operate to move vaginal discharge away from the head or absorbent area 174 of the tampon (FIGS. 18D–18F) and into the tampon body 182 where that discharge and its associated odors can be contained.

Figure 19A:
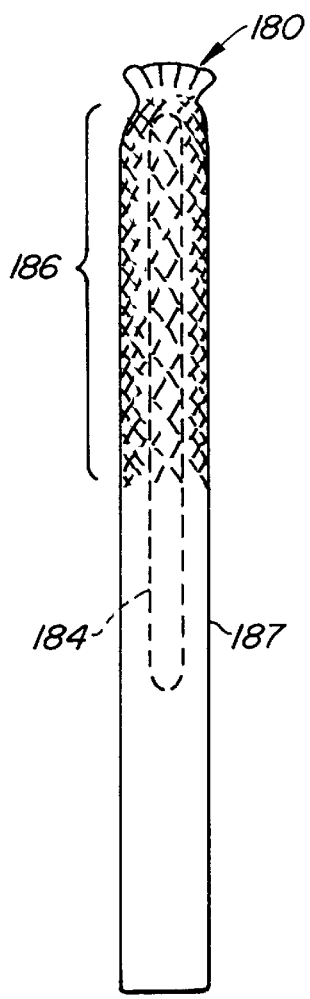
Figure 19B:
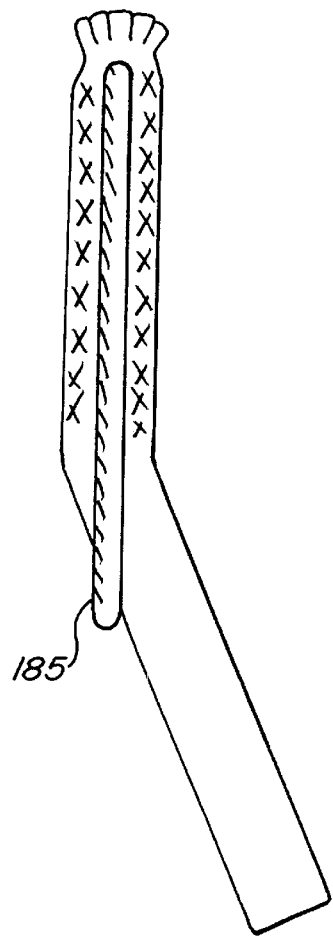
Figure 19C:
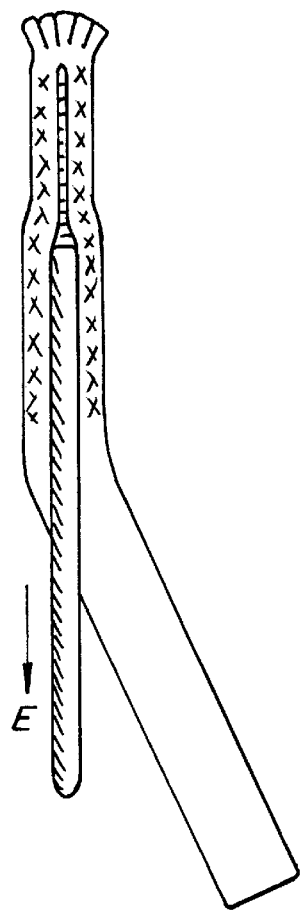

FIGS. 19A–19C show a further embodiment of the tampon 180 of FIGS. 18, illustrating the addition and use of an insertion rod 184. The insertion rod 180 is used to aid in insertion of the portion 186 of the tampon 180. As FIG. 19B illustrates, the lower portion 187 of the tampon 180 can be parted to expose the end 185 of the rod for its removal by pulling on the rod in the direction of arrow E (FIG. 19C). Preferably, the tampons shown in FIGS. 19A–19C are formed using any of the absorbent fiber constructions of FIGS. 1–2 and with conventional absorbent materials.

FIGS. 20 (20A–20E) illustrates yet another tampon that is similar to the tampon construction of FIGS. 18. As FIG. 20A shows, a tampon body 190 is formed by interweaving absorbent fibers of the invention—with or without conventional materials. The absorbent fibers of the body 190 are with apertures at 192 to permit fluid entry to the interior of the fibers. A swath of absorbent material 194 is constructed, and wrapped around the apertured portion of the length as shown in FIG. 20B. The length is then folded on itself, about the absorbent material 194, as shown in FIG. 20C, to produce an absorbent edge (i.e., at the ring 194) for fluid absorption. The distal ends 194a, 194b of the tampon 190 can be flattened match the shape of underwear. Leaving the insertion component 196 (FIG. 20E) with a cross-section such as the one depicted in FIG. 20F—viewed from cross-section A—A, of FIG. 20E. The now flattened ends 190a, 190b may be fitted with fabric end caps 198 to close the absorbent fibers of the construction and forming the unique tampon construction 190 shown in FIG. 20E. The ends 190a, 190b of the tampon 190, now formed as illustrated in FIG. 20E, may be folded or attached to undergarments (e.g., panties or underwear).

The constructions of the tampons shown in FIGS. 18–20 may be extended as shown in FIGS. 21 (21A, 21B, . . . , 21E). FIGS. 21 illustrated a tampon construction, designated generally with the reference numeral 200, in which the reservoir portion is split to form of the foldable pads 204a, 204b that depend from the insertion component 202. In addition to extending the absorbency of the tampon 200, the reservoir formed by the flaps 204 also operate to first protect the insertion component 202 by forming a protective containment until the tampon 200 is used. Later, the insertion component can be wrapped again by the flaps 204 for sanitary disposal. Thus, FIG. 21B shows the tampon 200 packaged by being folded in the flaps 204 unwrapped as shown in FIGS. 21A and 21C for insertion. After the tampon construction 200 is used, it may be refolded as shown in FIGS. 21E and 21C. During use, the absorbent pads 204a, 204b can be deployed laterally, as shown in FIG. 21A, or with both sides together, as in FIG. 21F.

Figure 21A:
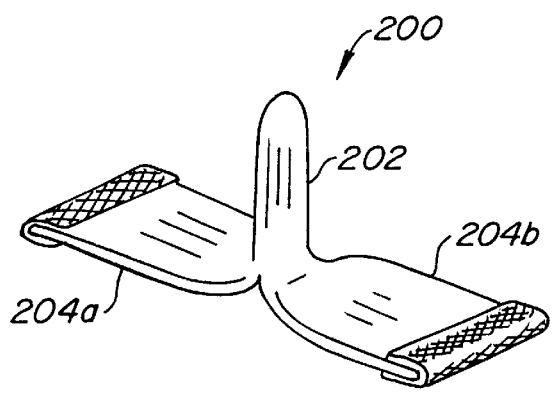
Figure 21B:
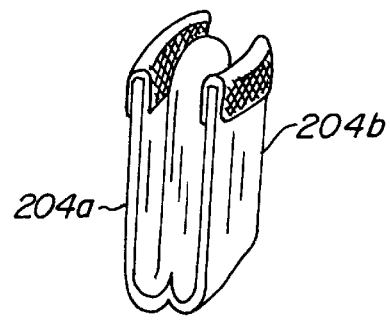
Figure 21C:
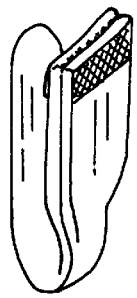
Figure 21D:
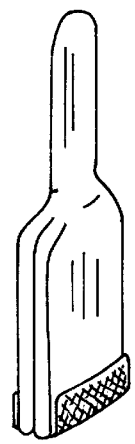
Figure 21E:
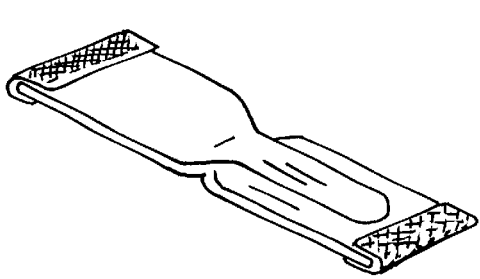
Figure 21F:
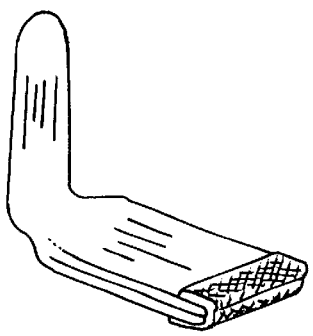
Figure 22A:
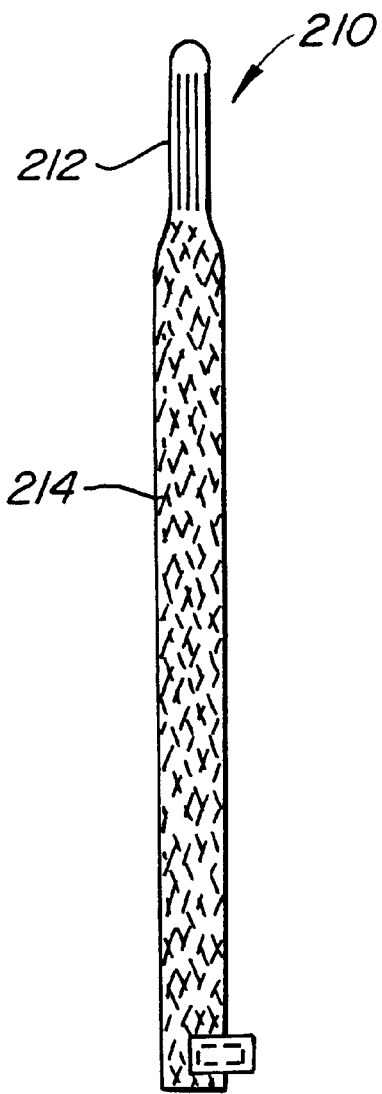
Figure 22B:
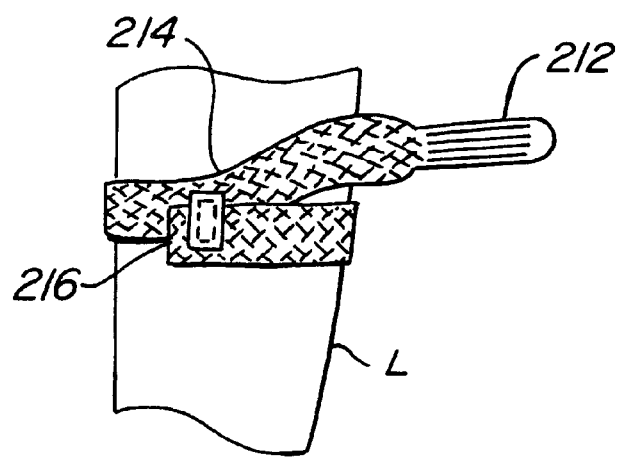

Turning now to FIGS. 22A and 22B, there is depict a tampon 210 formed from any of the absorbent fibers of the present invention. The tampon 210 includes an insertion component 212 and a rather lengthy reservoir component 214. The insertion component, as explained above, can be fabricated from conventional absorbent materials, or combined with absorbent fibers of the present invention, or fabricated solely from absorbent fibers. The reservoir component 214, of course, preferably is fabricated from absorbent fibers of a length that operates to extend the absorbing capability of the insertion component 212. The reservoir component 214 is of a length that allows it, when the tampon construction 210 is used, to be wound around t leg L of the user as illustrated in FIG. 21B. A Velcro brand type of attachment element 216 may be used to hold the reservoir component in place. The tampon construction 210 is particularly suitable for use by an invalid patient. An indicator 216 (FIG. 21B), such as a urine strip or other type of monitoring device, can be used to show when the absorbing capacity of the tampon construction 210 is near full by indicating when the indicator 216 first is exposed to liquids.

There has been disclosed herein an absorbent fiber construction capable of absorbing liquids by capillary action, and entraining the absorbed liquids to trap odors, and maintain a dry article. As should now be recognizable to those skilled in this art, the particular construction of the composite absorbent fiber of the present invention will allow its use with existing weaving and manufacturing techniques and technologies with little or no modification. Thus, the present invention can be adapted to present technologies to provide an absorbent article having greater absorbing capability than heretofore know.

Figure 23A:
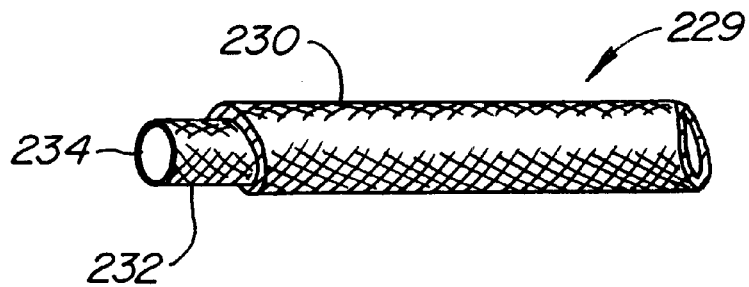
FIGS. 23A and 23B illustrate still further embodiments of the composite absorbent fiber of the present invention.

While a full and complete disclosure of the invention has been made, it will be apparent to those skilled in this art that various alternate modifications can be made without departing from the scope and content of the invention as defined in the claims. For example, the composite absorbent fiber may be constructed as shown in FIGS. 23. FIG. 23A illustrates a composite absorbent fiber 229 having an outer "skin" 230 of a highly absorbent material. The outer skin 230 covers an inner hollow element 232 made from a denser, less absorbent material. Fluid can be absorbed by the outer skin 230, transported to and through the inner element 232 to the hollow interior 234 thereof where it is transported by capillary action to a repository or reservoir.

In an alternative to the hollow inner element 232, it could be solid; that is, the element 232 would be a rod-like absorbent material, denser and less absorbent than the outer skin 230, but still capable of transporting liquid.

Figure 23B:
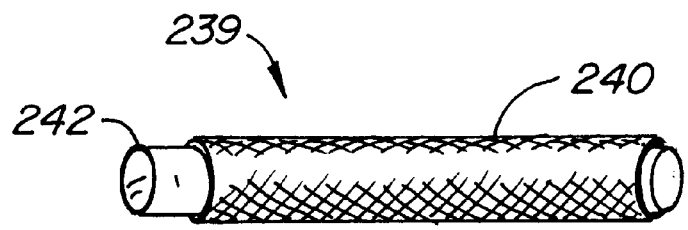

FIG. 23B shows further embodiment of this concept, illustrating a composite absorbent fiber 239, having an outer skin 240 fabricated from a highly absorbent material, and encasing a solid rod or filament 242 of plastic, glass, or similar material. Here, liquids are again transported by capillary action by the filament 242.

Figure 24:
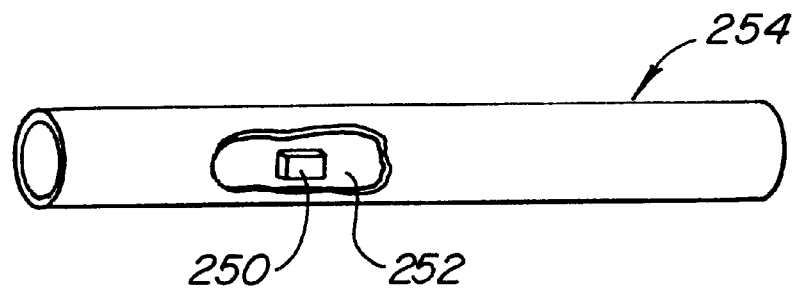
FIG. 24 illustrates use of a sensor or like device to monitor absorption of an absorbent fiber constructed according to the teachings of the present invention.

FIG. 24 illustrates placement of a sensor 250, such as a urine strip or other monitoring device—depending upon the particular liquid being absorbed—in the interior 252 of an absorbent fiber 254 constructed according to the teachings of the present invention. The sensor 250 may then operate to change color, and thereby color the outer surface of the absorbent fiber 254 when encountering a liquid absorbed by the fiber. The color can provide information of a capacity of the fiber (and other absorbent fibers used in conjunction with the fiber 254). Alternatively, the sensor or monitor 90 can be an electronic chip or device that is wired (or wirelessly) connected to monitoring equipment to communicate information about the liquid the sensor encounters during use of the absorbent fiber 254.

What is claimed is:

1. An absorbent fiber, comprising:

an elongate tube formed to have a hydrophobic exterior and an interior, the elongate tube having an opening formed for fluid ingress to the interior; and a cotton fiber contained in the interior.

2. The absorbent fiber of claim 1, wherein the elongate tube is formed from a plastic.

3. The absorbent fiber of claim 1, wherein the elongate tube is formed from a rubber material.

4. The absorbent fiber of claim 1, wherein the elongate tube is formed from a woven material.

5. The absorbent fiber of claim 4, wherein the opening is through the weave of the woven material.

6. An absorbent fiber, comprising:

an elongate tube formed to have a hydrophobic exterior and an interior, the elongate tube having an opening formed for fluid ingress to the interior, and a wool fiber contained in the interior.

7. The absorbent fiber of claim 6, wherein the elongate tube is formed from a plastic.

8. The absorbent fiber of claim 6, wherein the elongate tube is formed from a rubber material.

9. An absorbent fiber, comprising:

an elongate tube having an interior and an exterior, wherein the exterior is hydrophobic and is formed from a woven material, the elongate tube having an opening formed for fluid ingress to the interior; and a hydrophilic material contained in the interior.

10. The absorbent fiber of claim 9, wherein the hydrophilic material is cotton fiber.

11. The absorbent fiber of claim 9, wherein the hydrophilic material is wool fiber.

12. The absorbent fiber of claim 6, wherein the elongate tube is formed from a woven material.

13. The absorbent fiber of claim 12, wherein the opening is through the weave of the woven material.

\* \* \* \* \*